United States Patent
Kobayakawa et al.

(10) Patent No.: US 7,201,034 B2
(45) Date of Patent: Apr. 10, 2007

(54) GAS CONCENTRATION MEASUREMENT INSTRUMENT AND GAS CONCENTRATION MEASUREMENT METHOD

(75) Inventors: Tatsu Kobayakawa, Ibaraki (JP); Hideki Toda, Ibaraki (JP); Sachiko Saito, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 136 days.

(21) Appl. No.: 10/521,746

(22) PCT Filed: Jul. 18, 2003

(86) PCT No.: PCT/JP03/09200

§ 371 (c)(1),
(2), (4) Date: Jan. 19, 2005

(87) PCT Pub. No.: WO2004/010133

PCT Pub. Date: Jan. 29, 2004

(65) Prior Publication Data

US 2005/0235734 A1   Oct. 27, 2005

(30) Foreign Application Priority Data

Jul. 19, 2002 (JP) ............................. 2002-210512

(51) Int. Cl.
*G01N 29/02* (2006.01)
*G01N 29/22* (2006.01)
*G01N 29/44* (2006.01)

(52) U.S. Cl. .................. 73/24.01; 73/24.06; 73/31.01; 73/602

(58) Field of Classification Search ............... 73/24.01, 73/24.06, 31.01, 31.02, 31.03, 584, 602
See application file for complete search history.

(56) References Cited

FOREIGN PATENT DOCUMENTS

JP          8-136651        11/1994
JP          2002-5900       6/2000

OTHER PUBLICATIONS

International Search Report dated Oct. 28, 2003.

*Primary Examiner*—Daniel S. Larkin
(74) *Attorney, Agent, or Firm*—Reed Smith LLP; Stanley P. Fisher, Esq.; Juan Carlos A. Marquez, Esq.

(57) ABSTRACT

A gas concentration measurement instrument comprises: ultrasonic wave transmitting means for transmitting an ultrasonic wave according to an ultrasonic wave generation signal composed of a group of rectangular pulse waves; ultrasonic wave receiving means for converting the ultrasonic wave transmitted through the gas in the measurement region into an electric signal to use it as an ultrasonic wave reception signal; and gas concentration measuring means for measuring the signal output time when the ultrasonic wave generation signal is outputted, generating an envelope processing signal by subjecting the ultrasonic wave reception signal to an envelope extracting processing, measuring the threshold fall time when the envelope processing signal decreases below a predetermined threshold after exceeding the threshold, and measuring the difference between the threshold fall time and the signal output time as change in the gas concentration.

3 Claims, 9 Drawing Sheets

TIME DIFFERENCE MEASURING UNIT

GAS CONCENTRATION MEASUREMENT INSTRUMENT AND GAS CONCENTRATION MEASUREMENT METHOD

TECHNICAL FIELD

The present invention relates to a gas concentration measurement instrument for measuring change in concentration of gas in a measurement region and a gas concentration measurement method therefor.

BACKGROUND ART

A dielectric relaxation method for measuring the dielectric constant of a substance, an absorption spectrum measurement method for measuring the absorption distribution of an electromagnetic wave, and an ultrasonic propagating wave attenuation measurement method for measuring the amplitude damping factor of a passed ultrasonic wave can be used as a method for measuring gas concentration change and gas flow rate. Each of these methods does not have high time resolution.

On the other hand, a propagation time difference method for measuring the time of propagation of an acoustic wave from a transmitter to a receiver is a simple method, enabling the improvement of the time resolution. In this method, the transmitter transmits a standing wave such as a sine wave, the receiver receives the transmitted wave, the standing wave of the transmitter (transmitted wave) is compared with the signal from the receiver (received wave), a propagation time of the peak shift (phase difference) of these pulses is measured, and thus the propagation time corresponds to gas concentration change and gas flow rate.

DISCLOSURE OF THE INVENTION

However, there is a problem that when gas concentration change is measured using a standing wave as describe above, secondary and tertiary reflections of the standing wave occur and the measurement is impossible when the distance between ultrasonic wave transmitting and receiving units is less than 1 cm, and therefore gas concentration change in a tubule cannot be measured with this method.

In contrast, a gas concentration measurement instrument which solves the above problem has been developed and the instrument uses a rectangular pulse wave in place of the standing wave. In the method using a rectangular pulse wave, an ultrasonic wave generated based on a rectangular pulse wave is first received by an ultrasonic receiving element at the receiving side, the time difference between the time when a predetermined n-th wave from the first wave, for example, exceeds a threshold voltage and the first signal output time of the rectangular pulse wave is measured for the ultrasonic wave reception signal, and gas concentration change and gas flow rate in a measurement region that correspond to the time difference are outputted. However, the measurement point is positioned at a time period immediately after the ultrasonic wave reception element receives an acoustic wave and starts vibration. At the time period, the ultrasonic wave reception element still unstably operates and thus the measurement result is unstable. Conventionally, multiple measurements and the averaging are carried out to determine a central value and so measurements require time and the measurement work is made complicated.

The present invention has been proposed in view of the above problem and it is an object of the present invention to provide a gas concentration measurement instrument and a gas concentration measurement method therefor which can measure gas concentration change and suchlike even if the distance between ultrasonic wave transmitting and receiving units is less than 1 cm, and can obtain a highly accurate and stable measurement result only by one measurement.

To attain the above object, one aspect of the invention is characterized by a gas concentration measurement instrument for measuring change in concentration of gas in a measurement region, comprising: ultrasonic wave transmitting means for transmitting an ultrasonic wave according to an ultrasonic wave generation signal composed of a group of rectangular pulse waves; ultrasonic wave receiving means for converting the ultrasonic wave transmitted through the gas in the measurement region into an electric signal to use it as an ultrasonic wave reception signal; and gas concentration measuring means for measuring the signal output time when the ultrasonic wave generation signal is outputted, generating an envelope processing signal by subjecting the ultrasonic wave reception signal to an envelope extracting processing, measuring the threshold fall time when the envelope processing signal decreases below a predetermined threshold after exceeding the threshold, and measuring the difference between the threshold fall time and the signal output time as an indication of change in the gas concentration.

Another aspect of the invention is characterized by a gas concentration measurement method for measuring change in concentration of gas in a measurement region, comprising: transmitting an ultrasonic wave according to an ultrasonic wave generation signal composed of a group of rectangular pulse waves; converting the ultrasonic wave transmitted through the gas in the measurement region into an electric signal to use it as an ultrasonic wave reception signal; and measuring the signal output time when the ultrasonic wave generation signal is outputted, generating an envelope processing signal by subjecting the ultrasonic wave reception signal to an envelope extracting process, measuring the threshold fall time when the envelope processing signal decreases below a predetermined threshold after exceeding the threshold, and measuring the difference between the threshold fall time and the signal output time as an indication of change in the gas concentration.

BEST MODE FOR CARRYING OUT THE INVENTION

A preferred embodiment of the present invention will be described below with reference to the accompanying drawings.

Figure 1:
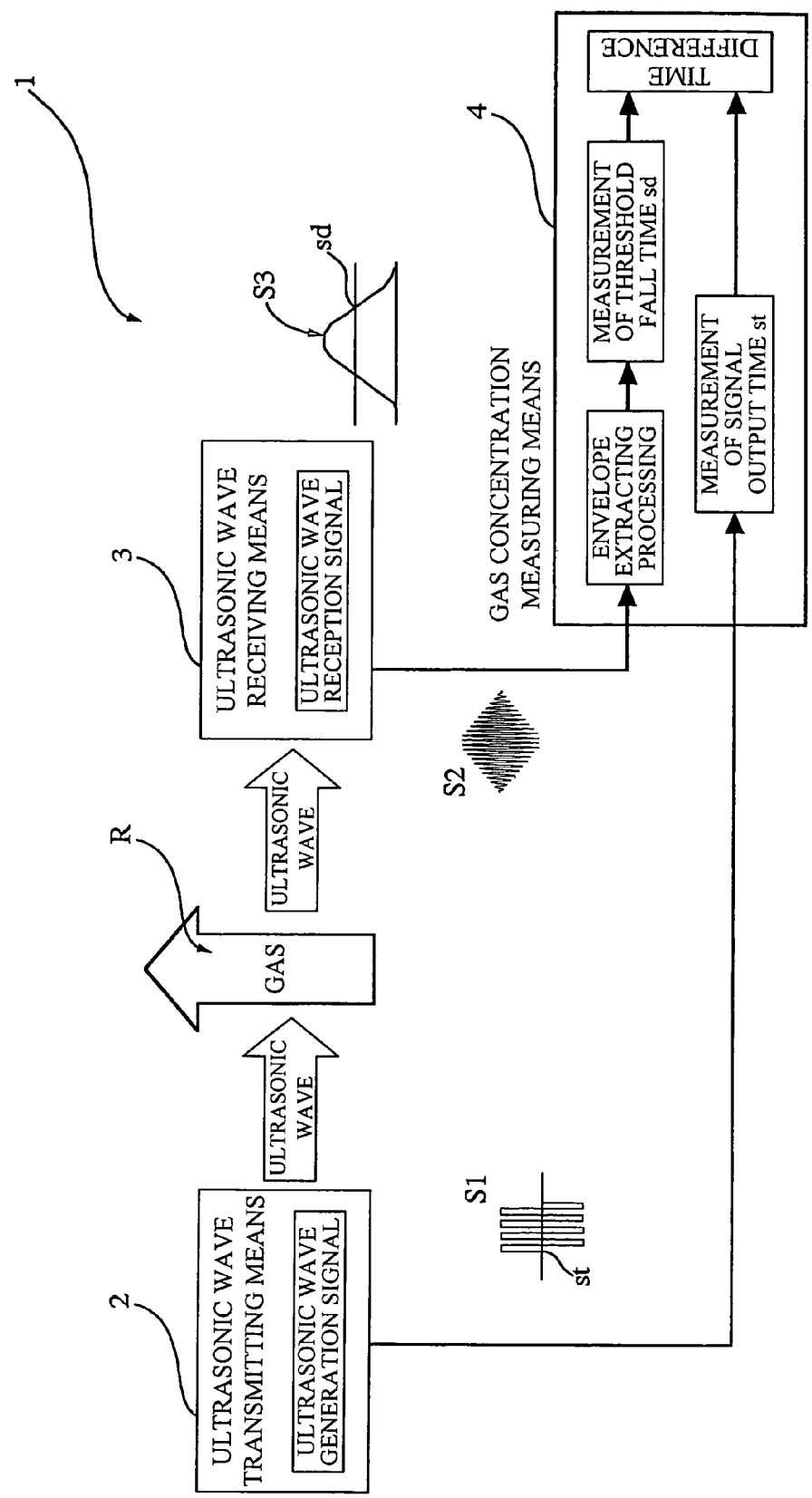
FIG. 1 is a block diagram of a gas concentration measurement instrument of the present invention.

FIG. 1 is a block diagram of a gas concentration measurement instrument of the present invention. In the figure, the gas concentration measurement instrument 1 of the present invention measures change in concentration of gas in a measurement region R. The gas concentration measurement instrument 1 comprises ultrasonic wave transmitting means 2 for transmitting an ultrasonic wave according to an ultrasonic wave generation signal S1 composed of a group of rectangular pulse waves; ultrasonic wave receiving means 3 for converting the ultrasonic wave transmitted through the gas in the measurement region R into an electric signal to use it as an ultrasonic wave reception signal S2; and gas concentration measuring means 4 for measuring the signal output time st when the ultrasonic wave generation signal S1 is outputted, generating an envelope processing signal by subjecting the ultrasonic wave reception signal S2 to an envelope extracting processing, measuring the threshold fall time sd when the envelope processing signal decreases below a predetermined threshold after exceeding the threshold, and measuring the difference between the threshold fall time and the signal output time st as change in the gas concentration.

A more specific description will be made below with reference to FIGS. 2 through 7.

Figure 2:
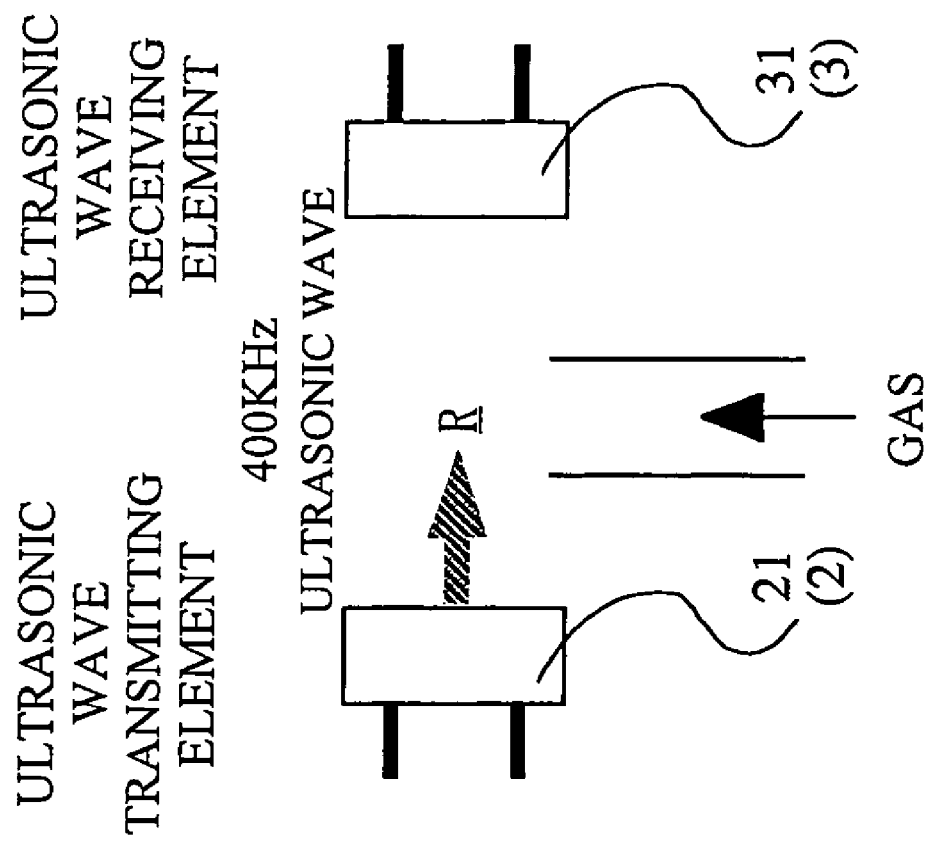
FIG. 2 shows an example of the configuration of substantial parts around a measurement region.

FIG. 2 shows an example of the configuration of substantial parts around a measurement region. As shown in the figure, the above mentioned ultrasonic wave transmitting means 2 and ultrasonic wave receiving means 3 comprises an ultrasonic wave transmitting element 21 and an ultrasonic wave receiving element 31, respectively, each of which is composed of, for example, a piezoelectric element. The ultrasonic wave transmitting element 21 transmits, for example, a 400 KHz ultrasonic wave according to an ultrasonic wave generation signal S1. The ultrasonic wave passes through the measurement region R where, for example, air and nitrogen flow alternatively, is received by the ultrasonic wave receiving element 31, is converted into an electric signal and then is outputted for use as an ultrasonic wave reception signal S2.

Figure 3:
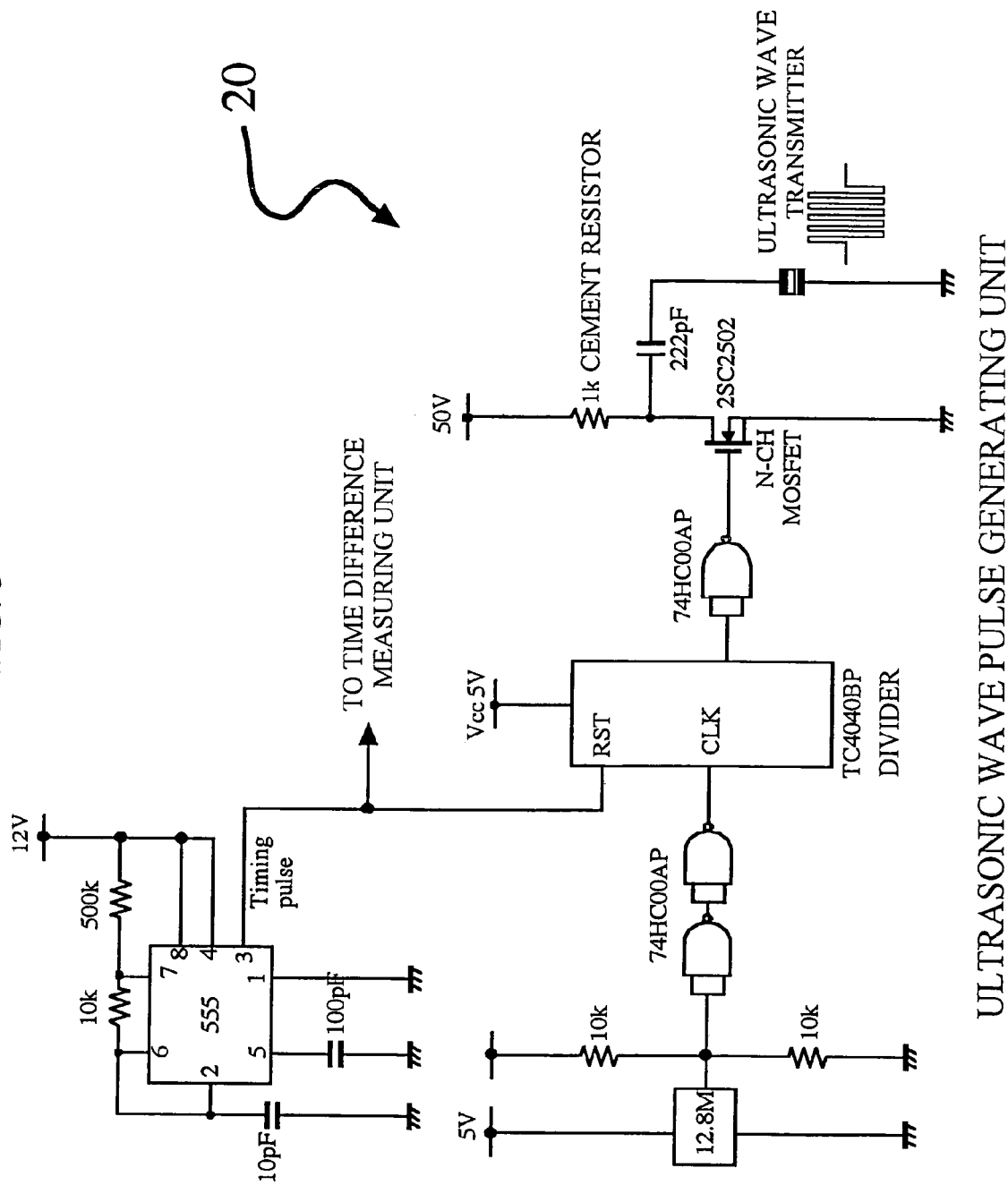
FIG. 3 is a circuit diagram showing an ultrasonic pulse transmitting unit in the gas concentration measurement instrument.
Figure 4:
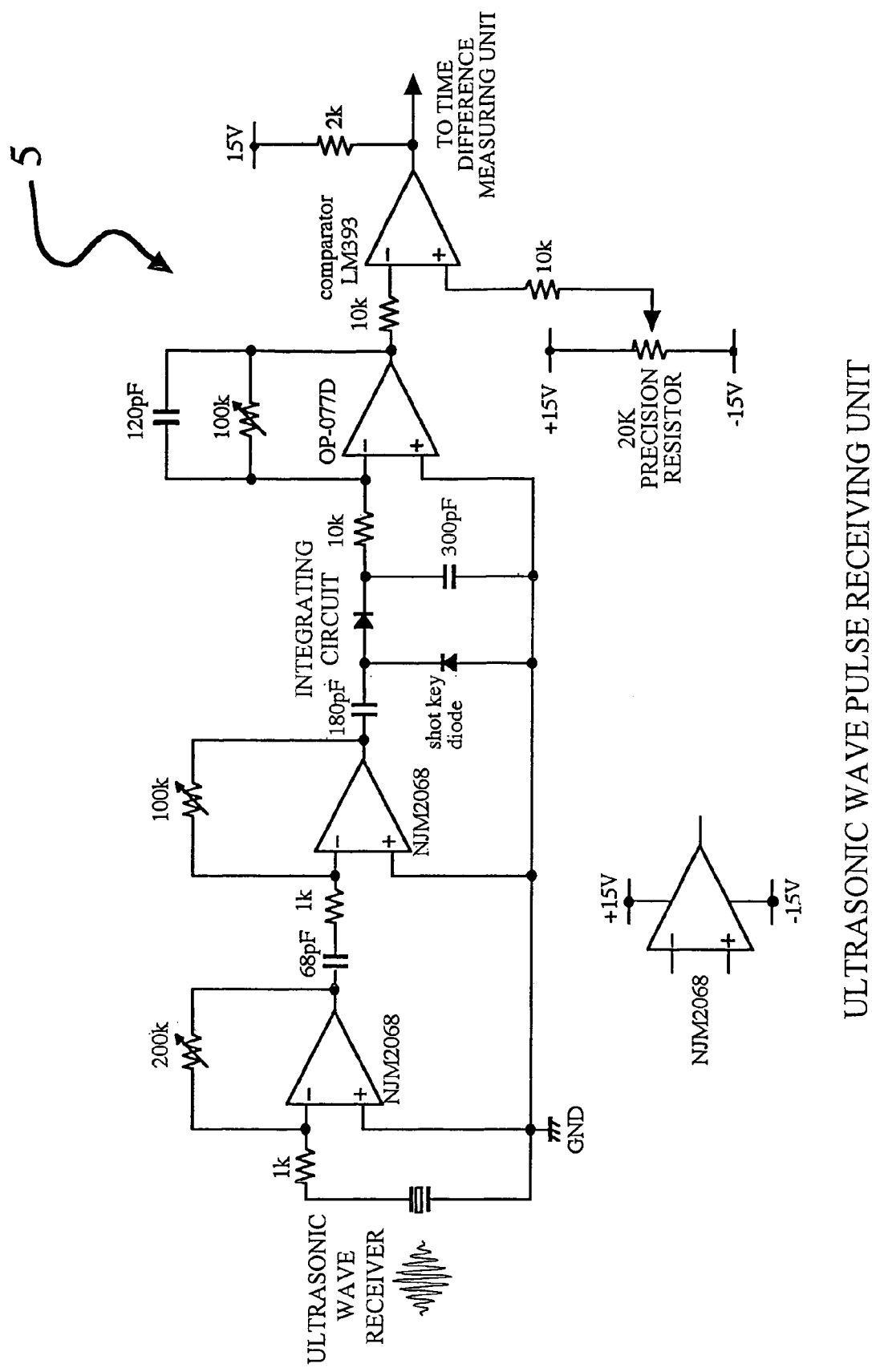
FIG. 4 is a circuit diagram showing an ultrasonic pulse receiving unit in the gas concentration measurement instrument.
Figure 5:
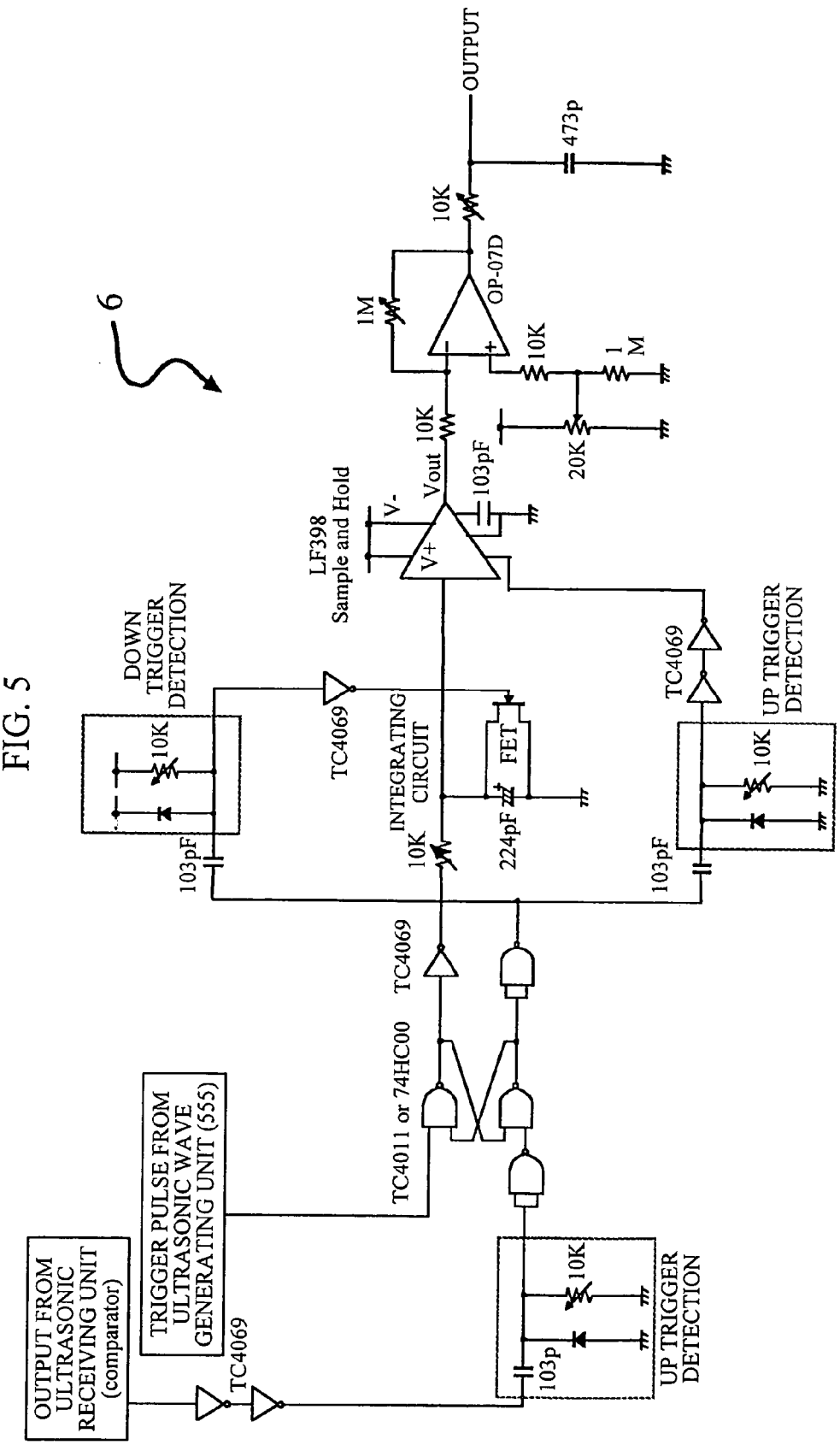
FIG. 5 is a circuit diagram showing a time difference measuring unit in the gas concentration measurement instrument.
Figure 6:
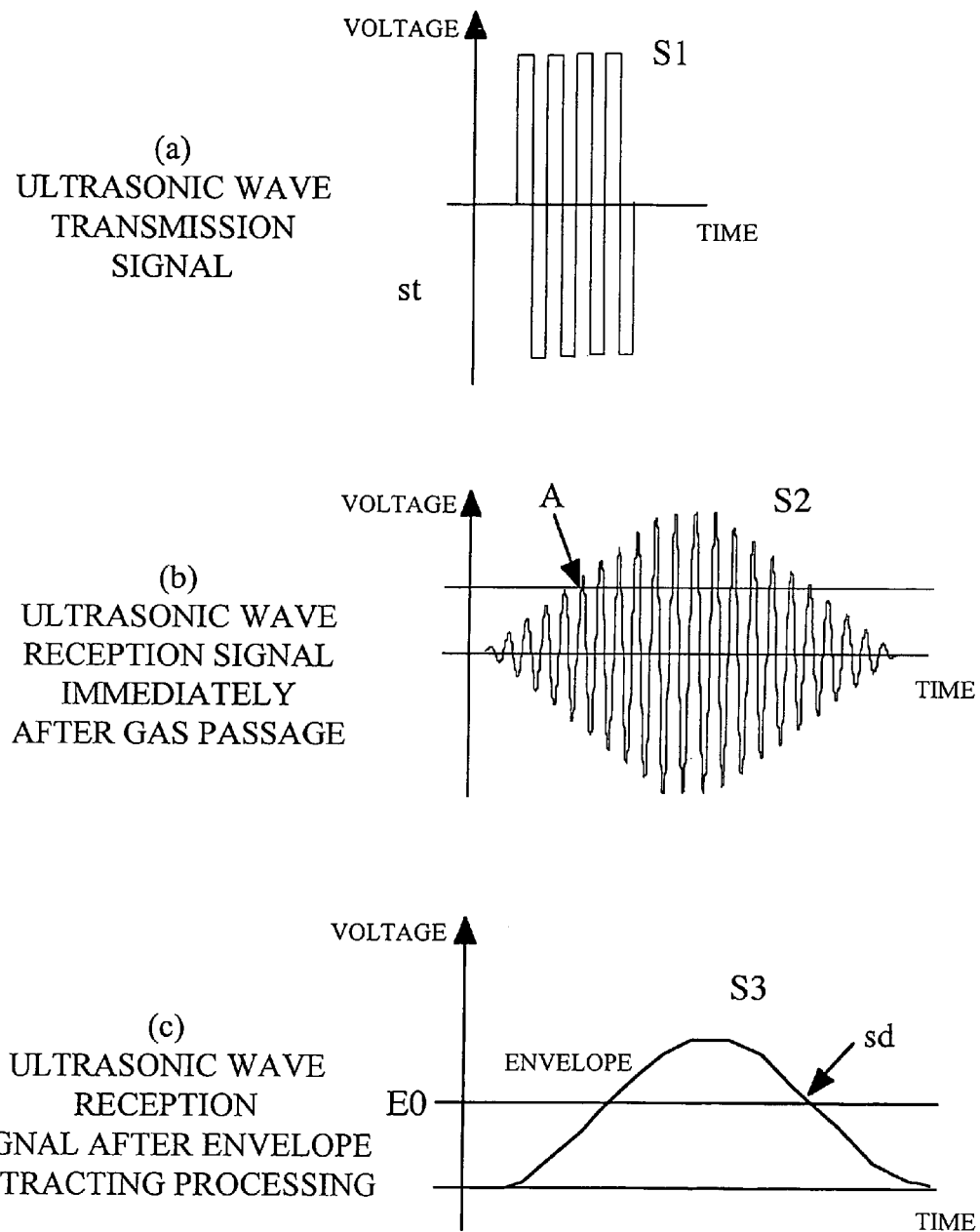
FIG. 6 shows signal waveforms in predetermined parts of the gas concentration measurement instrument.

FIG. 3 is a circuit diagram showing an ultrasonic pulse transmitting unit in the gas concentration measurement instrument; FIG. 4 is a circuit diagram showing an ultrasonic pulse receiving unit in the gas concentration measurement instrument; FIG. 5 is a circuit diagram showing a time difference measuring unit in the gas concentration measurement instrument; and FIG. 6 shows signal waveforms in predetermined parts of the gas concentration measurement instrument.

The gas concentration measurement instrument 1 of the present invention uses, as shown in FIG. 6(a), a rectangular pulse wave group S1 composed of plural (for example, a few to ten) rectangular pulse waves having a predetermined cycle when an ultrasonic wave is generated. The rectangular pulse wave group (ultrasonic wave generation signal) S1 is generated by an ultrasonic wave pulse generating unit 20 shown in FIG. 3, and is inputted to the ultrasonic wave transmitting element 21 of the final stage, and then an ultrasonic wave is outputted according to vibration of the ultrasonic wave transmitting element 21. The ultrasonic wave generation signal S1, branched and obtained from a signal line between a timer IC (555) and a divider in the ultrasonic wave pulse generating unit 20, is outputted to a time difference measuring unit 6 in FIG. 5.

In contrast, an ultrasonic wave passing through the measurement region R and influenced by the gas is received by the ultrasonic wave receiving element 31 in the ultrasonic wave pulse receiving unit 5 and the received ultrasonic wave is converted into an electric signal to be an ultrasonic wave reception signal S2 as shown in FIG. 6(b). After that, the ultrasonic wave pulse receiving unit 5 subjects the ultrasonic wave reception signal S2 to an envelope extracting process using a low pass filter and generates an envelope processing signal S3 as shown in FIG. 6(c). Moreover, the ultrasonic wave pulse receiving unit 5 uses a comparator to make a comparison between the envelope processing signal S3 and a threshold voltage E0. Then, the unit 5 detects a threshold fall time sd when the envelope processing signal S3 decreases below the threshold voltage E0 after exceeding the threshold voltage E0, and outputs the threshold fall time sd to the time difference measuring unit 6.

When the ultrasonic wave generation signal S1 is inputted to the time difference measuring unit 6, the time difference measuring unit 6 measures the first signal output time st of the ultrasonic wave generation signal S1. And, the unit 6 measures the time difference between the threshold fall time sd and the signal output time st and outputs the time difference as an indication of change in gas concentration.

Among means 2, 3, and 4 shown in FIG. 1, ultrasonic wave transmitting means 2 corresponds to an ultrasonic wave pulse generating unit 20; ultrasonic wave receiving means 3 corresponds to an ultrasonic wave receiving element 31 in the ultrasonic wave pulse receiving unit 5; and gas concentration measuring means 4 corresponds to the ultrasonic wave pulse generating unit 20 and a time difference measuring unit 6 at a stage after the ultrasonic wave receiving element 31.

As described above, the gas concentration measurement instrument 1 of the present invention has been configured to measure the time difference between the threshold fall time sd of the envelope processing signal S3 and the first signal output time st of the ultrasonic wave generation signal S1. The time difference indicates a value depending on gas concentration change and gas flow rate change in the measurement region R. The measurement of the time difference therefore can improve the accuracy of measuring the gas concentration change and gas flow rate change in the measurement region R. Now, the threshold fall time sd is positioned in a region where the ultrasonic wave reception signal S2 attenuates to be stable, so that the measurement result is also stable. Processing such as averaging required for maintaining data accuracy is therefore not needed, and gas concentration change can be measured with a single ultrasonic wave transmission-reception, and the gas concentration change can therefore be measured at short times and at once.

Since the invention uses a rectangular pulse wave to generate an ultrasonic wave, no secondary and tertiary reflections occur although they occur in the case where a standing wave is used to generate an ultrasonic wave. Even if the distance between the ultrasonic wave transmitting element 21 and ultrasonic wave receiving element 31 is made short into several millimeters or so, measurement can be made, and gas concentration change and gas flow rate in a tubule can be measured with a high degree of accuracy.

The time when a predetermined n-th wave from the first wave for ultrasonic wave reception signal S2 exceeds a threshold voltage (point A in FIG. 6(b)) or the time when it exceeds the threshold voltage first after envelope extracting processing is performed is conventionally specified as acoustic wave arrival time. And, the time difference between the acoustic wave arrival time and the signal output time st is measured, and the time difference is conventionally outputted for use as gas concentration change and gas flow rate in a measurement region R. However, the vicinity of the time when the ultrasonic wave receiving element 31 receives an acoustic wave and starts vibrating (vicinity of point A in FIG. 2) is unstable, and so conventionally an algorithm of "n-th wave is detected" as described above is used for the measurement. Even when a measurement is made actually based on the algorithm, the measurement result is still unstable, and so multiple measurements and the averaging are carried out to determine a central value. This means an unstable signal is obtained by sacrificing the time resolution.

In contrast, the inventor finds that the ultrasonic wave receiving element 31 is unstable in the former part where the element starts receiving an acoustic wave as described above, but is very stable (blurring is hard to occur under the same experiment) in the latter part (where a received wave (ultrasonic wave reception signal S2) attenuates), and the stable latter part is used for measurement. In the present invention, a low pass filter is used to first extract a received wave envelope and the envelope fall (not rise) time sd is detected. The time when the envelope processing signal exceeds the threshold voltage E0 is not measured, but the time when the envelope processing signal decreases below the threshold voltage E0 is measured. As a result, a single ultrasonic wave transmission-reception with no processing such as averaging enables the measurement of gas concentration change and gas flow rate.

Actual measurement results are described below with reference to FIG. 7, FIG. 8, and FIG. 9.

Figure 7:
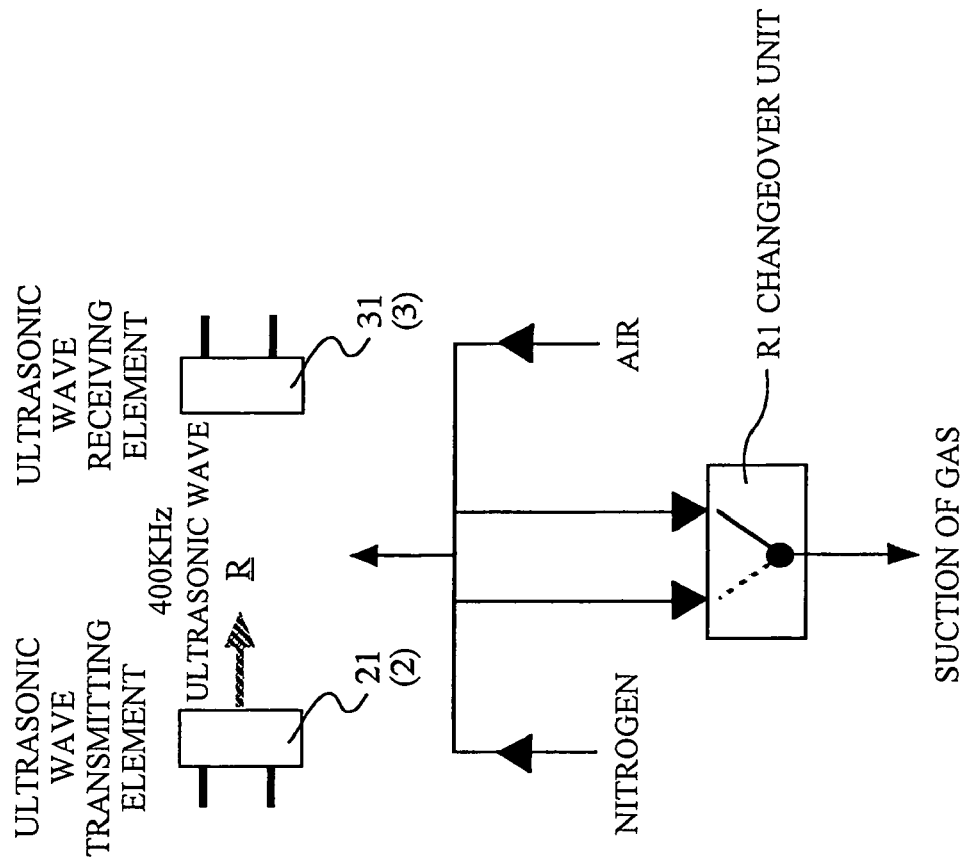
FIG. 7 shows an example of the configuration of a gas changeover apparatus.
Figure 8:
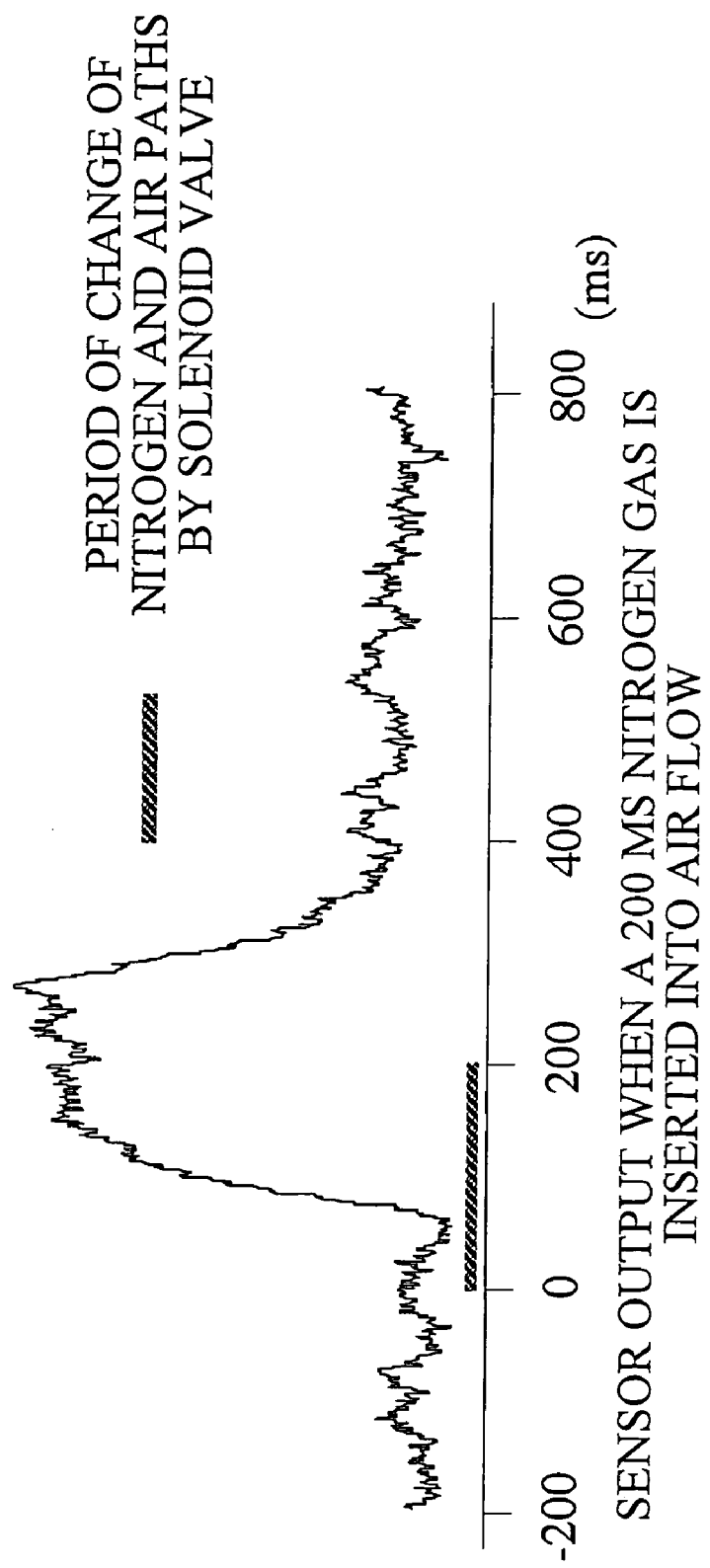
FIG. 8 shows a result obtained by changing gases in the measurement region using the gas changeover apparatus shown in FIG. 7 and measuring change in the gas concentration with the gas concentration measurement instrument of the present invention.

FIG. 7 shows an example of the configuration of a gas changeover apparatus; and FIG. 8 shows a result obtained by changing gases in the measurement region using the gas changeover apparatus shown in FIG. 7 and measuring change in the gas concentration with the gas concentration measurement instrument of the present invention.

In FIG. 7, both air and nitrogen can always flow into a measurement region R. When a changeover unit R1 is, for example, connected to the air side and air is suctioned from the changeover unit R1, only nitrogen flows into the measurement region R. And, the gas concentration measurement instrument 1 transmits an ultrasonic wave from the ultrasonic wave transmitting element 21 and allows passage of gas in the measurement region R to measure change in concentration of the gas.

Here, nitrogen is first suctioned by the changeover unit R1 to supply air to the measurement region R, and in this state, solenoid value changeover at the changeover unit R1 then suctions air and supplies nitrogen of only 200 ms to measure gas concentration change at the changeover time. The distance between the ultrasonic wave transmitting element 21 and the ultrasonic wave receiving element 31 is specified as 3 m. FIG. 8 shows the result of the measurement made only once and clearly indicates that with only this single measurement, changeover to nitrogen begins from after 50 ms elapses and changeover is completed for about 150 ms. Compared with the results of measuring contrast between carbon dioxide of molecular weight 44 and air of molecular weight 28.8 using a conventional standing wave (results of arithmetic means at 30 times), the measurement of the present invention is made as follows: nitrogen of molecular weight 28 and air of molecular weight 28.8, that is, gasses of proximate molecular weights are measured and the measurement achieves higher S/N ratio than a conventional measurement although it is made only once.

Figure 9:
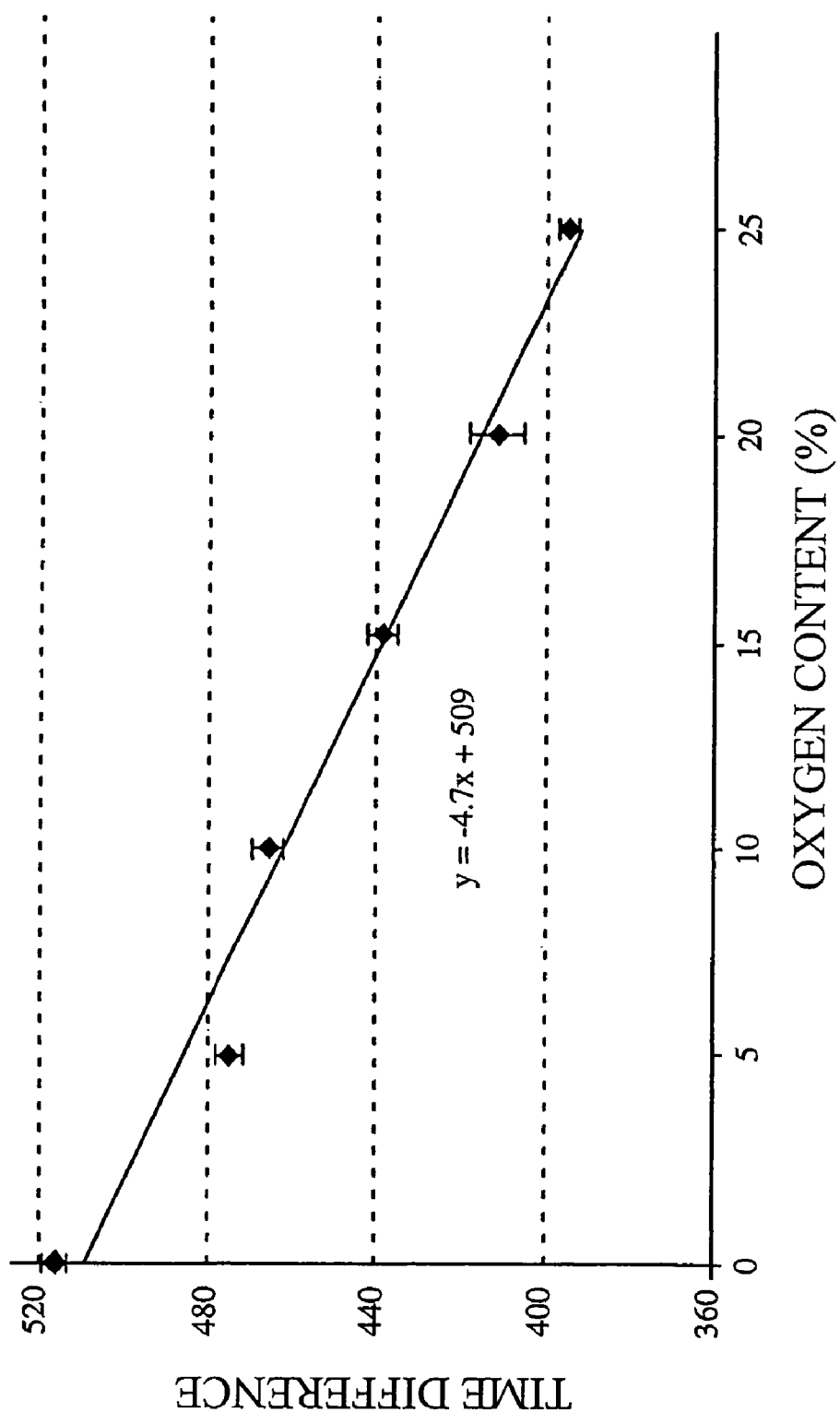
FIG. 9 shows a result obtained by changing gases in the measurement region using the gas changeover apparatus shown in FIG. 7 and measuring change in the gas mixture ratio with the gas concentration measurement instrument of the present invention.

FIG. 9 shows the results of measurement of the time difference between the threshold fall time sd and the signal output time st when oxygen and nitrogen are flown using the gas changeover apparatus in FIG. 7 to vary a percentage of the oxygen to 0% (nitrogen: 100%), 5%, 10%, 15%, 20% (air), and 25%. Since the gas concentration measurement instrument 1 of this invention detects the threshold fall time sd positioned at the latter of the ultrasonic wave reception signal S2 to measure the time difference, stable measurement is made at high accuracy and at high speed and therefore, the time difference linearly responds to gas mixture ratio (composition ratio) as shown in FIG. 9. Such linear response to gas mixture ratio change can be observed in a method using a conventional standing wave and a method using the former of an ultrasonic wave reception signal. It is therefore found that the gas concentration measurement instrument 1 can also measure gas mixture ratio (composition ratio) stably at high accuracy and at high speed.

The present invention capable of highly accurate, fast, and stable measurement of gas concentration change enables measurement of changes in fluid in a chemical plant, engine, and suchlike at high time resolution.

The above describes the case where air and nitrogen or oxygen and nitrogen flows alternately in the measurement region R, but the gases are not limited to air and nitrogen, and any gases can be accepted.

INDUSTRIAL APPLICABILITY

As described above, the present invention measures the time difference between the threshold fall time of an envelope processing signal and the signal output time of an ultrasonic wave generation signal. Since the threshold fall time is positioned in a region where the ultrasonic wave reception signal attenuates to be stable, the measurement result is also stable. Processing such as averaging required for maintaining data accuracy is therefore not needed, and gas concentration change can be measured by a single ultrasonic wave transmission-reception. The gas concentration change can therefore be measured at short times and fast.

Since a rectangular pulse wave is used to generate an ultrasonic wave, no secondary and tertiary reflections occur although they occur when a conventional standing wave is used. Even if the distance between an ultrasonic wave transmitting element and an ultrasonic receiving element is shortened to about several millimeters, measurement can be made, and thus gas concentration change and gas flow rate change in a tubule can be measured at high accuracy.

What is claimed is:

1. A gas concentration measurement instrument for measuring change in concentration of gas in a measurement region, comprising:
    ultrasonic wave transmitting means for transmitting an ultrasonic wave composed of a group of rectangular pulse waves as an ultrasonic wave generation signal;
    ultrasonic wave receiving means for receiving an ultrasonic wave transmitted through the gas in the measurement region and converting the ultrasonic wave transmitted through the gas in the measurement region into an electric signal to use it as an ultrasonic wave reception signal; and gas concentration measuring means for measuring a signal output time when the ultrasonic wave generation signal is outputted, generating an envelope processing signal by subjecting the ultrasonic wave reception signal to an envelope extracting process, measuring a threshold fall time when the envelope processing signal decreases below a predetermined threshold after exceeding the threshold, and measuring the difference between the threshold fall time and the signal output time as an indication of change in the gas concentration.

2. The gas concentration measurement instrument according to claim 1, wherein the difference between the threshold fall time and the signal output time linearly responds to the gas mixture ratio.

3. A gas concentration measurement method for measuring change in concentration of gas in a measurement region, comprising:

transmitting an ultrasonic wave composed of a group of rectangular pulse waves through a gas in a measurement region as an ultrasonic wave generation signal;

receiving the ultrasonic wave transmitted through the gas in the measurement region;

converting the ultrasonic wave transmitted through the gas in the measurement region into an electric signal to use it as an ultrasonic wave reception signal; and measuring a signal output time when the ultrasonic wave generation signal is outputted, generating an envelope processing signal by subjecting the ultrasonic wave reception signal to an envelope extracting process, measuring a threshold fall time when the envelope processing signal decreases below a predetermined threshold after exceeding the threshold, and measuring the difference between the threshold fall time and the signal output time as an indication of change in the gas concentration.

* * * * *